United States Patent
Morschhäuser et al.

(10) Patent No.: US 7,053,146 B2
(45) Date of Patent: May 30, 2006

(54) COMPOSITIONS CONTAINING COPOLYMERS BASED ON ACRYLOYLDIMETHYL AMINOETHYLSULFONIC ACID AND SYNERGISTIC ADDITIVES

(75) Inventors: Roman Morschhäuser, Mainz (DE); Christoph Kayser, Mainz (DE); Matthias Löffler, Nledernhausen (DE); Karl Heinz Heier, Frankfurt am Main (DE); Aranka Tardi, Neuberg (DE); Manfred Schade, Bonsecours (FR); Gernold Botthof, Antrifftal (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/433,119

(22) PCT Filed: Nov. 28, 2001

(86) PCT No.: PCT/EP01/13859

§ 371 (c)(1),
(2), (4) Date: Nov. 24, 2003

(87) PCT Pub. No.: WO02/44230

PCT Pub. Date: Jun. 6, 2002

(65) Prior Publication Data

US 2004/0109838 A1   Jun. 10, 2004

(30) Foreign Application Priority Data

| Dec. 1, 2000 | (DE) | 100 59 818 |
| Dec. 1, 2000 | (DE) | 100 59 819 |
| Dec. 1, 2000 | (DE) | 100 59 821 |
| Dec. 1, 2000 | (DE) | 100 59 822 |
| Dec. 1, 2000 | (DE) | 100 59 823 |
| Dec. 1, 2000 | (DE) | 100 59 824 |
| Dec. 1, 2000 | (DE) | 100 59 825 |
| Dec. 1, 2000 | (DE) | 100 59 826 |
| Dec. 1, 2000 | (DE) | 100 59 827 |
| Dec. 1, 2000 | (DE) | 100 59 828 |
| Dec. 1, 2000 | (DE) | 100 59 829 |
| Dec. 1, 2000 | (DE) | 100 59 830 |
| Dec. 1, 2000 | (DE) | 100 59 831 |
| Dec. 1, 2000 | (DE) | 100 59 832 |
| Dec. 1, 2000 | (DE) | 100 59 833 |
| Jun. 11, 2001 | (DE) | 101 27 876 |

(51) Int. Cl.
*C08K 3/20*   (2006.01)

(52) U.S. Cl. ............... 524/461; 524/458; 524/747; 524/755; 526/243; 526/245; 526/247; 526/248; 526/279; 526/287; 526/288; 526/292.2; 526/292.6; 526/312

(58) Field of Classification Search .............. 526/243, 526/245, 247, 248, 287, 288, 279, 292.2, 526/292.6, 312; 524/458, 461, 747, 755
See application file for complete search history.

(56) References Cited

U.S. PATENT DOCUMENTS

| 3,931,089 A | 1/1976 | Karl .................... 260/29.65 Q |
| 4,521,578 A | 6/1985 | Chen et al. .................. 526/288 |
| 4,859,458 A | 8/1989 | Salamone et al. |
| 5,292,843 A * | 3/1994 | Jenkins et al. ........... 526/318.5 |
| 5,368,850 A | 11/1994 | Cauwet et al. ................ 424/70 |
| 5,639,841 A * | 6/1997 | Jenkins ...................... 526/333 |
| 5,688,514 A | 11/1997 | Chaudhry et al. |
| 5,879,718 A | 3/1999 | Sebillote-Arnaud ......... 424/705 |
| 6,120,780 A | 9/2000 | Dupuis et al. .............. 424/401 |
| 6,395,853 B1 | 5/2002 | Oswald et al. |
| 6,468,549 B1 | 10/2002 | Dupuis et al. .............. 424/401 |
| 6,645,476 B1 * | 11/2003 | Morschhauser et al. ... 424/70.1 |
| 6,727,318 B1 * | 4/2004 | Mathauer et al. ........... 524/801 |
| 2004/0109838 A1 | 6/2004 | Morschhauser |

FOREIGN PATENT DOCUMENTS

| EP | 0 356 241 | 2/1990 |
| EP | 0 815 828 | 1/1998 |
| EP | 0 815 845 | 1/1998 |
| EP | 0 816 403 | 1/1998 |
| EP | 0815 844 | 1/1998 |
| EP | 1089142 | 1/2001 |
| WO | WO 98/00094 | 1/1998 |
| WO | WO 0244230 | 6/2002 |

OTHER PUBLICATIONS

English Translationof International Preliminary Examination Report, PCT/EP01/13859, Dated Feb. 26, 2003.

* cited by examiner

*Primary Examiner*—Helen L. Pezzuto
(74) *Attorney, Agent, or Firm*—Richard P. Silverman

(57) ABSTRACT

The invention relates to compositions comprising copolymers based on acryloyldimethyltaurine and also synergistic additives selected from anionic, cationic, nonionic, and betaine surfactants. The compositions exhibit a pronounced thermoassociative behavior and are outstandingly suitable as thickeners. The copolymers of the present invention are useful in formulating cosmetics, pharmaceuticals, and oil field chemicals.

33 Claims, No Drawings

COMPOSITIONS CONTAINING COPOLYMERS BASED ON ACRYLOYLDIMETHYL AMINOETHYLSULFONIC ACID AND SYNERGISTIC ADDITIVES

DESCRIPTION

Compositions comprising copolymers based on acryloyldimethyltaurine and synergistic additives.

The invention relates to compositions comprising copolymers based on acryloyldimethyltaurine and also synergistic additives selected from anionic, cationic, nonionic, and betaine surfactants. The compositions exhibit a pronounced thermoassociative behavior and are outstandingly suitable as thickeners. In recent years water-soluble polymers have acquired a continually increasing importance in industry and science. In volume terms, polyelectrolytes are occupying a very large proportion of the overall annual production. They find application, for example, in paper processing, in the laundry detergents industry, in textile processing, in crop protection, in petroleum extraction or as important base materials for cosmetics.

In the cosmetics sector a continually growing importance has been attached to polyelectrolytes for fifteen years. Besides water-soluble surface-active substances there is a high demand in this sector for systems which thicken oil and water. Thickeners of this kind, particularly the "superabsorbents" prepared on the basis of polyacrylic acid, have progressed since their development in the 1970s to become a pillar of the hygiene sector. In their crosslinked versions, partly or fully neutralized polyacrylic acids and their water-soluble copolymers are employed in numerous cosmetic formulations as bodying agents. The diversity of possible structures and the diverse possible applications associated therewith are manifested not least in a host of patents filed worldwide since the mid-1970s.

In the 1990s, innovative thickeners based on 2-acrylamido-2-methyl-1-propanesulfonic acid (AMPS) and their salts were introduced into the market (EP 816 403 and WO 98/00094). In both homopolymer and copolymer form (®Aristoflex AVC, Clariant GmbH) such thickeners are superior in many respects to the corresponding polycarboxylates (Carbopols). For example, thickener systems based on AMPS display outstanding properties in pH ranges below pH 6, i.e., in a pH range in which it is no longer possible to operate with conventional polycarboxylate thickeners. Moreover, the microgel structure inherent in the acryloyldimethyltaurine thickeners leads to a particularly pleasant skin sensation. The ease of processing and the favorable toxicological profile of the principal monomer imbue these thickeners with a high application potential.

Over recent years representatives of a new thickener design have entered the market. In these thickeners, two different properties have been combined in one polymer, thereby opening up new fields of application. Thickening emulsifiers or dispersants are but two examples of this new class of substance. Brand names that may be mentioned include the Pemulens® TR-1 and TR-2 from BF Goodrich or the Aculyn® products from Rohm & Haas. All existing versions are based on hydrophobically modified versions of the conventional polyacrylates.

Surprisingly it has been found that copolymers based on acryloyldimethyltaurine (ADMT) and/or acryloyldimethyltaurates in combination with what are called synergistic additives, selected from anionic, cationic, betaine, and nonionic surfactants, display a reversible thermoassociative effect in aqueous and organic-aqueous media, which above certain threshold temperatures leads to a sharp increase in viscosity.

Compositions comprising the copolymers and the synergistic additives are outstandingly useful as thickeners. An advantage is that this thermoviscosification is also realizable in formulations with a high electrolyte content.

The invention provides compositions comprising

I) at least one water-soluble or water-swellable copolymer obtainable by free-radical copolymerization of
  A) acryloyldimethyltaurine and/or acryloyldimethyltaurates,
  B) if desired, one or more olefinically unsaturated, noncationic, optionally crosslinking, optionally heat-sensitive, comonomers containing at least one oxygen, nitrogen, sulfur or phosphorus atom and possessing a molecular weight of less than 500 g/mol,
  C) if desired, one or more olefinically unsaturated, cationic comonomers containing at least one oxygen, nitrogen, sulfur or phosphorus atom and possessing a molecular weight of less than 500 g/mol,
  D) if desired, one or more at least monofunctional, silicon-containing components capable of free-radical polymerization,
  E) if desired, one or more at least monofunctional, fluorine-containing components capable of free-radical polymerization,
  F) if desired, one or more, optionally heat-sensitive, macromonomers having a number-average molecular weight of greater than or equal to 200 g/mol,
  G) the copolymerization taking place in the presence or absence of at least one polymeric additive having number-average molecular weights of from 200 g/mol to $10^9$ g/mol,
  H) with the proviso that component A) is copolymerized with at least one component selected from groups B) to G), with at least one of the structural elements selected from groups B) to G) possessing heat-sensitive properties;

and

II) at least one synergistic additive selected from anionic, cationic, nonionic, and betaine surfactants.

The copolymers preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyl-dimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals which if desired may be occupied by up to 3 $(C_2-C_{10})$-hydroxyalkyl groups. Preference is also given to mono- to triethoxylated ammonium compounds with a different degree of ethoxylation. It should be noted that the invention also embraces mixtures of two or more of the abovementioned representatives or the free acryloyldimethyltaurine.

The degree of neutralization of the acryloyldimethyltaurine in the copolymers can be between 0 and 100%, particular preference being given to a degree of neutralization of more than 80%.

Based on the total mass of the copolymers, the amount of acryloyldimethyltaurine and/or acryloyldimethyltaurates can be from 0.1 to 99.9% by weight, preferably from 20 to 99.5% by weight, more preferably from 50 to 98% by weight.

As comonomers B) it is possible to use all olefinically unsaturated noncationic monomers whose reaction parameters allow copolymerization with acryloyl-dimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 22.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be $(C_1–C_{22})$-alkyl radicals which may optionally be occupied by up to 3 $(C_2–C_{10})$-hydroxyalkyl groups. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethyl-acrylamide, N,N-diethylacrylamide, and N,N-di-isopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The skilled worker will understand that some of the monomers listed here lead to heat-sensitive properties in the polymer, so that the corresponding polymers possess LCST and/or UCST properties. The following nonlimiting list shows the most well-known monomers which can give rise to copolymers having heat-sensitive properties: N,N-diisopropylacrylamide, N-vinylpyrrolidone (NVP), methacrylic acid, and vinyl acetate and/or vinyl alcohol units in the polymer.

In one further preferred embodiment the copolymers are crosslinked, i.e., they contain comonomers B) containing at least two polymerizable vinyl groups.

Preferred crosslinkers are methylenebisacrylamide; methylenebismethacrylamide; esters of unsaturated monocarboxylic and polycarboxylic acids with polyols, preferably di-acrylates and triacrylates and -methacrylates, more preferably butanediol and ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA). The weight fraction of the comonomers B), based on the total mass of the copolymers, can be from 0 to 99.9% by weight and is preferably from 0.05 to 80% by weight, more preferably from 0.05 to 70% by weight.

Suitable comonomers C) include all olefinically unsaturated monomers with cationic charge which are capable of forming copolymers with acryloyldimethyl-taurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine structure.

Comonomers C) for the purposes of the invention are also amino-functionalized precursors which can be converted into their corresponding quaternary derivatives by polymer-analogous reactions (e.g., reaction with DMS).
Particularly preferred comonomers C) are diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride and/or
N-methyl-4-vinylpyridinium chloride.

The weight fraction of the comonomers C), based on the total mass of the copolymers, is preferably from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicon-containing components D) are those of formula (I).

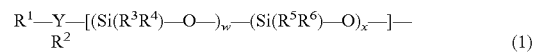

(1)

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl, methacryloyl, crotonyl, senecionyl, itaconyl, maleyl, fumaryl or styryl radical, more preferably an acryloyl or methacryloyl radical.

The attachment of the silicone-containing polymer chain to the reactive end group $R^1$ requires a suitable chemical bridge Y. Preferred bridges Y are —O—, —C(O)—, —C(O)—O—, —S—, —O—$CH_2$—CH(O—)—C $H_2OH$, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—$(C_1–C_{50})$alkenyl-O—, —O—phenyl-O—, —O-benzyl-O—, —O—$(C_5–C_8)$cycloalkyl-O—, —O—($C_1$–$C_{50}$)alkenyl-O—, —O—(CH($CH_3$)—$CH_2$—O)$_n$—, —O—($CH_2$—$CH_2$—O)$_n$—, —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. The polymeric central moiety is represented by silicone-containing repeating units. $R^3$, $R^4$, $R^5$, and $R^6$ denote independently of one another —$CH_3$, —O—$CH_3$, —$C_6H_5$ or —O—$C_6H_5$.

The indices w and x in the above formula represent stoichiometric coefficients which amount independently of one another to from 0 to 500, preferably 10 to 250. The distribution of the repeating units across the chain can be not only purely random but also blocklike, alternating or gradientlike.

$R^2$ stands for an aliphatic, olefinic, cycloaliphatic, arylaliphatic or aromatic ($C_1$–$C_{50}$) hydrocarbon radical (linear or branched) or —OH, —$NH_2$, —N($CH_3$)$_2$, —$R^7$ or for the structural unit [—Y—$R^1$]. The definition of the two variables Y and $R^1$ has already been explained. $R^7$ stands for an Si-containing group, preferably for —O—Si($CH_3$)$_3$, —O—Si(Ph)$_3$, —O—Si(O—Si($CH_3$)$_3$)$_2$$CH_3$) or —O—Si(O—Si(Ph)$_3$)$_2$Ph).

If $R^2$ is an element of the group [—Y—$R^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicon-containing components D) are the following compounds with acrylic or methacrylic modification:

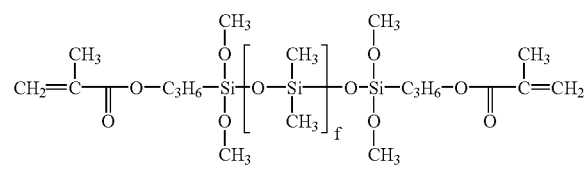

methacryloyloxypropyldimethylsilyl-endblocked polydimethylsiloxanes with f=10 to 500, preferably 10 to 250;

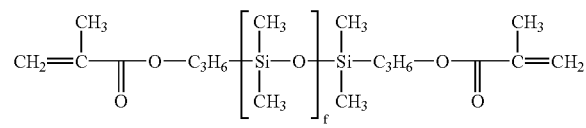

methacryloyloxypropyl-endblocked polydimethylsiloxanes with f=10 to 500, preferably 10 to 250; and

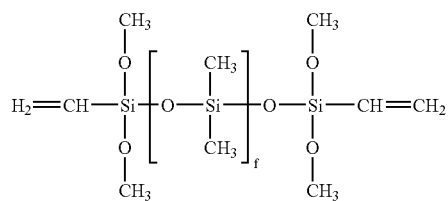

vinyldimethoxysilyl-endblocked polydimethylsiloxanes with f=10–500, preferably 10 to 250.

Based on the total mass of the copolymers, suitable silicon-containing components can be present in a fraction of up to 99.8% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked. Preferred fluorine-containing components E) are those of formula (II).

$$R^1—Y—C_rH_{2r}C_sF_{2s}CF_3 \quad (II)$$

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$–$C_{50}$)alykl-O—, —O-phenyl-O—, —O-benzyl-O—, —O—($C_5$–$C_8$)cycloalkyl—O—, —O—($C_1$–$C_{50}$)alkenyl-O—, —O—(CH($CH_3$)—$CH_2$—O)$_n$—, —O—($CH_2$—$CH_2$—O)$_n$—, and —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluorooctylethanol methacrylate,
perfluorooctylpropanol methacrylate,
perfluorohexylethanolyl polyglycol ether methacrylate,
perfluorohexoylpropanolyl poly[ethylglycol-co-propylene glycol ether] acrylate,
perfluorooctylethanolyl poly[ethylglycol-block-co-propylene glycol ether] methacrylate,
perfluorooctylpropanolyl polypropylene glycol ether methacrylate.

Based on the total mass of the copolymers the fraction of fluorine-containing components can be up to 99.8% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers.

Preferred macromonomers F) are compounds of formula (III).

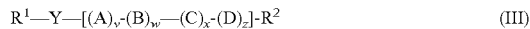

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl, methacryloyl, crotonyl, senecionyl, itaconyl, maleyl, fumaryl or styryl radical. Attachment of the polymer chain to the reactive end group requires a suitable bridging group Y. Preferred bridges Y are —O—, —C(O)—, —C(O)—O—, —S—, —O—CH$_2$—CH(O—)—CH$_2$OH, —O—CH$_2$—CH(OH)—CH$_2$O—, —O—SO$_2$—O—, —O—SO$_2$—O—, —O—SO—O—, —PH—, —P(CH$_3$)—, —PO$_3$—, —NH—, and —N(CH$_3$)—, more preferably —O—.

The polymeric central moiety of the macromonomer is represented by the discrete repeating units A, B, C, and D. Preferably but without limitation the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate (vinyl alcohol), N-vinylpyrrolidinone, N-vinylcaprolactam, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be ≧1.

The distribution of the repeating units over the macromonomer chain can be random, blocklike, alternating or gradientlike.

$R^2$ denotes a linear or branched aliphatic, olefinic, cycloaliphatic, arylaliphatic or aromatic (C$_1$–C$_{50}$) hydrocarbon radical, OH, —NH$_2$, —N(CH$_3$)$_2$ or is the structural unit [—Y—R$^1$].

In the case of $R^2$ being [—Y—R$^1$] the macromonomers in question are difunctional and suitable for crosslinking the copolymers.

Particularly preferred macromonomers F) are acrylically or methacrylically monofunctionalized alkyl ethoxylates of formula (IV).

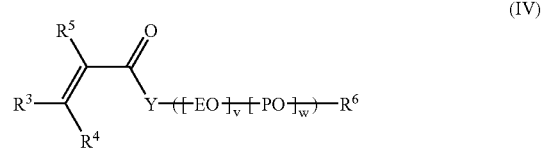

$R_3$, $R_4$, $R_5$, and $R_6$ are independently of one another hydrogen or n-aliphatic, iso-aliphatic, olefinic, cycloaliphatic, arylaliphatic or aromatic (C$_1$–C$_{30}$) hydrocarbon radicals.

Preferably $R_3$ and $R_4$ are H or —CH$_3$, more preferably H; $R_5$ is H or —CH$_3$; and $R_6$ is an n-aliphatic, iso-aliphatic, olefinic, cycloaliphatic, arylaliphatic or aromatic (C$_1$–C$_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average ≧1. The distribution of the EO and PO units over the macromonomer chain can be random, blocklike, alternating or gradientlike. Y stands for the above-mentioned bridges.

Particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030-methacrylate | H | H | —CH$_3$ | -lauryl | 3 | 0 |
| ® LA-070-methacrylate | H | H | —CH$_3$ | -lauryl | 7 | 0 |
| ® LA-200-methacrylate | H | H | —CH$_3$ | -lauryl | 20 | 0 |
| ® LA-250-methacrylate | H | H | —CH$_3$ | -lauryl | 25 | 0 |
| ® T-080-methacrylate | H | H | —CH$_3$ | -talc | 8 | 0 |
| ® T-080-acrylate | H | H | H | -talc | 8 | 0 |
| ® T-250-methacrylate | H | H | —CH$_3$ | -talc | 25 | 0 |
| ® T-250-crotonate | —CH$_3$ | H | —CH$_3$ | -talc | 25 | 0 |
| ® OC-030-methacrylate | H | H | —CH$_3$ | -octyl | 3 | 0 |
| ® OC-105-methacrylate | H | H | —CH$_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —CH$_3$ | —CH$_3$ | H | -behenyl | 10 | 0 |
| ® PEG-440-diacrylate | H | H | H | -acryloyl | 10 | 0 |
| ® B-11-50-methacrylate | H | H | —CH$_3$ | -butyl | 17 | 13 |
| ® MPEG-750-methacrylate | H | H | —CH$_3$ | -methyl | 18 | 0 |
| ® P-010-acrylate | H | H | H | -phenyl | 10 | 0 |
| Polyglycol-B-1100-methacrylate | H | H | —CH$_3$ | -butyl | 25 | 0 |
| Polyglycol-OC-1100-methacrylate | H | H | —CH$_3$ | -octyl | 25 | 0 |
| ® MPEG-1000-methacrylate | H | H | —CH$_3$ | -methyl | 25 | 0 |
| ® MPEG-2000-methacrylate | H | H | —CH$_3$ | -methyl | 45 | 0 |
| ® O-050-acrylate | H | H | H | -oleyl | 5 | 0 |

Further, particularly suitable macromonomers F) are esters of (meth)acrylic acid with ($C_{10}$–$C_{18}$) fatty alcohol polyglycol ethers having 8 EO units (Genapol® C-080)

$C_{11}$ oxo alcohol polyglycol ethers having 8 EO units (Genapol® UD-080)

($C_{12}$–$C_{14}$) fatty alcohol polyglycol ethers having 7 EO units (Genapol® LA-070)

($C_{12}$–$C_{14}$) fatty alcohol polyglycol ethers having 11 EO units (Genapol® LA-110)

($C_{16}$–$C_{18}$) fatty alcohol polyglycol ethers having 8 EO units (Genapol® T-080)

($C_{16}$–$C_{18}$) fatty alcohol polyglycol ethers having 15 EO units (Genapol® T-150)

($C_{16}$–$C_{18}$) fatty alcohol polyglycol ethers having 11 EO units (Genapol® T-110)

($C_{16}$–$C_{18}$) fatty alcohol polyglycol ethers having 20 EO units (Genapol® T-200)

($C_{16}$–$C_{18}$) fatty alcohol polyglycol ethers having 25 EO units (Genapol® T-250)

($C_{18}$–$C_{22}$) fatty alcohol polyglycol ethers having 25 EO units and/or iso-($C_{16}$–$C_{18}$) fatty alcohol polyglycol ethers having 25 EO units.

The Genapol® grades are products of Clariant GmbH.

The skilled worker understands that some of the monomers listed here lead to heat-sensitive properties in the copolymers, so that the corresponding polymers possess LCST and/or UCST properties.

The following nonlimiting list represents macromonomers which can give rise to copolymers having heat-sensitive properties.

Acryloyl- or methacryloyl-fatty alcohol ethoxylate esters, such as, for example:

($C_{10}$–$C_{18}$) fatty alcohol polyglycol ethers having 8 EO units (Genapol® C-080), $C_{11}$ oxo alcohol polyglycol ethers having 8 EO units (Genapol® UD-080), ($C_{12}$–$C_{14}$) fatty alcohol polyglycol ethers having 7 EO units (Genapol® LA-070), ($C_{16}$–$C_{18}$) fatty alcohol polyglycol ethers having 8 EO units (Genapol® T-080), ($C_{16}$–$C_{18}$) fatty alcohol polyglycol ethers having 25 EO units (Genapol® T-250), iso-($C_{16}$–$C_{18}$) fatty alcohol polyglycol ethers having 25 EO units or polyglycol-B-1100-methacrylate, polyglycol-OC-1100-methacrylate, ®MPEG-1000-acrylate, ®MPEG-2000-methacrylate, ®MPEG-5000-methacrylate or vinylically modified poly(diisopropylacrylamides), polyvinyl alcohols, polyvinylpyrrolidinones and/or polyvinylcaprolactams.

The molecular weight of the macromonomers F) is preferably from 200 g/mol to $10^6$ g/mol, more preferably from 200 to $10^5$ g/mol, and very preferably from 200 to 10 000 g/mol.

Based on the total mass of the copolymers it is possible to use suitable macromonomers at up to 99.8% by weight. Preference is given to employing the ranges from 0.5 to 30% by weight and from 70 to 99.5% by weight. Particularly preferred are fractions of from 1 to 20% by weight and from 65 to 95% by weight.

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention.

Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols. The term "copolymers" also comprehends those having more than two different monomer types.

Particularly preferred additives G) are homopolymers and copolymers of vinyl acetate, vinylbutyral, vinyl alcohol, N-vinylformamide, N-vinylacetamide, N-vinylpyrrolidone, ethylene oxide, propylene oxide, acryloyldimethyltaurine, N-vinylcaprolactone, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

For the preparation of the copolymers the polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

The polymerization reaction can be conducted, for example, as a precipitation polymerization, emulsion polymerization, bulk polymerization, solution polymerization or gel polymerization. Particularly advantageous for the profile of properties of the copolymers is precipitation polymerization, preferably in tert-butanol.

Essential to the invention is the fact that the copolymers (component I)) in combination with what are termed the synergistic additives (component II)) display an unexpectedly pronounced thermoassociative behavior.

The synergistic additives may be anionic, cationic, non-ionic and/or betaine surfactants.

Only the combination of copolymers and synergistic additives leads, above certain threshold temperatures, to the unexpectedly pronounced development of thermoreversible, associative superstructures and hence to a sharp increase in viscosity.

Surprisingly the skilled worker is substantially free in the selection of the synergistic additives, although an advantage is that it is possible to control the threshold temperature and the extent of the thermoassociative effect by way of the choice of the copolymer/additive combinations.

Preferred synergistic additives are polyalkylene glycols (preferably PEGs and MPEGs, PO/EO copolymers), alkylpolyglycols (preferably ®Genapol grades, Clariant GmbH), alkylsulfonates, preferably laurylsulfonate, ether sulfates, preferably alkyl ether sulfates, more preferably lauryl ether sulfate, alkyl quats, preferably behenyl quats (preferably ®KDMP, Clariant GmbH), cocoamidopropyl-betaine (preferably ®Genagen CAB, Clariant), alkyldimethylbetaine (preferably ®Genagen LAB, Clariant GmbH), and mixtures of ether sulfates and betaines.

Naturally, combinations of two or more representatives of the abovementioned classes of substance are also in accordance with the invention.

Particularly preferred synergistic additives are polyalkylene glycols, very preferably PEGs and MPEGs, and alkylpolyglycols, very preferably the ®Genapol grades. Preferred PEGs and MPEGs are those having molecular weights above 300 g/mol and water-soluble alkylpolyglycols having $(C_2-C_{22})$-alkyl chains.

In the compositions of the invention the weight ratio between copolymers and synergistic additives is preferably from 1:1 000 to 1 000:1, more preferably from 1:100 to 100:1, very preferably from 1:10 to 10:1, with particular preference from 1:5 to 5:1.

The compositions of the invention contain preferably from 0.01 to 50% by weight, more preferably from 0.1 to 25% by weight, very preferably from 0.1 to 10% by weight, with particular preference from 0.1 to 5% by weight of copolymers of component I) and from 0.01 to 50% by weight, more preferably from 0.1 to 25% by weight, very preferably from 0.1 to 10% by weight, with very particular preference from 0.1 to 5% by weight of synergistic additives of component II).

Surprisingly it has been found that the thermoassociative effect of the compositions of the invention can be controlled very effectively by way of the salt content of the compositions. The compositions contain preferably from 0.1 to 25% by weight, more preferably from 1 to 10% by weight, very preferably from 1 to 5% by weight of salt. A preferred salt is sodium chloride.

Through the great structural diversity of the copolymers and the diverse possibilities for combination with the synergistic additives, the compositions of the invention possess very broad-spectrum possibilities for use, and can be tailored to virtually any task where interface effects and/or surface effects play a part.

The compositions of the invention are preferably oilfield chemicals, cosmetic compositions, dermatological compositions, pharmaceutical compositions, detergents, and crop protection compositions.

The invention further provides for the use of the compositions of the invention as thickeners.

The invention further provides a method of thickening media, which comprises adding at least one of the compositions of the invention to the media.

The invention further provides a method of thickening media comprising at least one of the copolymers which comprises adding at least one of the synergistic additives to the media.

The invention likewise provides a method of thickening media comprising at least one of the synergistic additives which comprises adding at least one of the copolymers to the media.

In the context of their use in accordance with the invention and of the methods of the invention for the thickening of media the compositions of the invention and/or the individual components I) and II) can also be used in concentrated form, where appropriate in the form of a single-substance mixture or as single substances. In that case the amounts for use are preferably calculated such that the final concentrations of components I) and II) in the resulting media correspond to the preferred values indicated above.

The following examples serve to illustrate the invention without, however, restricting it thereto.

EXAMPLES 1 to 9:

Examples 1 to 9 relate to the copolymers. In combination with synergistic additives the copolymers form heat-sensitive structures which above certain threshold temperatures allow the formation of associative structures.

EXAMPLE 1

| Reactants | amount (g) |
| --- | --- |
| $NH_3$-neutralized AMPS | 80 |
| Genapol-LA-070-methacrylate | 10 |
| TMPTA | 1.8 |
| t-Butanol | 500 |
| Dilauroyl peroxide (initiator) | 1 |

The polymer was prepared by the precipitation method in tert-butanol. The monomers in t-butanol were introduced as an initial charge and the reaction mixture was rendered inert, and then, after initial heating, the reaction was initiated by addition of DLP. The polymer was isolated by removing the solvent under suction and by subsequent vacuum drying.

EXAMPLE 2

| Reactants | amount (g) |
|---|---|
| NH$_3$-neutralized AMPS | 80 |
| Genapol-LA-070-methacrylate | 10 |
| t-Butanol | 500 |
| Dilauroyl peroxide (initiator) | 1 |

The polymer was prepared by the precipitation method in tert-butanol. The monomers in t-butanol were introduced as an initial charge and the reaction mixture was rendered inert, and then, after initial heating, the reaction was initiated by addition of DLP. The polymer was isolated by removing the solvent under suction and by subsequent vacuum drying.

EXAMPLE 3

| Reactants | amount (g) |
|---|---|
| NH$_3$-neutralized AMPS | 70 |
| N-Vinylpyrrolidone | 5 |
| ® Genapol-T-250-methacrylate | 15 |
| [2-(Methacryloyloxy)ethyl]trimethylammonium chloride | 10 |
| Water | 500 |
| Na$_2$S$_2$O$_8$ (initiator) | 1 |
| Poly-N-vinylpyrrolidone (® K-30, BASF) | 10 |

The polymer was prepared by the gel polymerization method in water. The monomers were dissolved in water, the reaction mixture was rendered inert, and then, after initial heating, the reaction was initiated by addition of sodium peroxodisulfate. The polymer gel was subsequently comminuted and the polymer was isolated by vacuum drying.

EXAMPLE 4

| Reactants | amount (g) |
|---|---|
| AMPS | 60 |
| ® Genapol-LA-250-methacrylate | 10 |
| ® Genapol-T-250-acrylate | 10 |
| [2-(Methacrylamido)ethyl]trimethylammonium chloride | 20 |
| Cyclohexane | 200 |
| Water | 300 |
| Span 80 | 1 |
| Na$_2$S$_2$O$_8$ (initiator) | 1 |

The polymer was prepared by the emulsion method in water. The monomers were emulsified in water/cyclohexane using ®Span 80, the reaction mixture was rendered inert using N$_2$, and then, after initial heating, the reaction was initiated by addition of sodium peroxodisulfate. The polymer emulsion was subsequently evaporated down (cyclohexane acting as azeotrope former for water) and by this means the polymer was isolated.

EXAMPLE 5

| Reactants | amount (g) |
|---|---|
| NH$_3$-neutralized AMPS | 60 |
| ® MPEG-2000-methacrylate | 20 |
| Methacryloyloxypropyldimethicone (® GP-478, Genesee Pol. Corp.) | 10 |
| Perfluorooctyl polyethylene glycol methacrylate | 5 |
| t-Butanol | 500 |
| AIBN (initiator) | 1 |

The polymer was prepared by the precipitation method in tert-butanol. The monomers in t-butanol were introduced as an initial charge and the reaction mixture was rendered inert, and then, after initial heating, the reaction was initiated by addition of AIBN. The polymer was isolated by removing the solvent under suction and by subsequent vacuum drying.

EXAMPLE 6

| Reactants | amount (g) |
|---|---|
| Na-neutralized AMPS | 80 |
| N-Vinylformamide | 5 |
| ® Genapol-O-150-methacrylate | 5 |
| Water | 300 |
| MBA | 1.8 |
| H$_2$O$_2$/iron (initiator) | 1 |

The polymer was prepared by the solution method in water. The monomers were dissolved in water, the reaction mixture was rendered inert, and then, after initial heating, the reaction was initiated by means of a suitable redox couple. The polymer solution was subsequently evaporated down and the polymer was then isolated by vacuum drying.

EXAMPLE 7

| Reactants | amount (g) |
|---|---|
| NH$_3$-neutralized AMPS | 70 |
| ® Genapol-T-250-acrylate | 10 |
| Monofunctionalized (methacrylically) ethoxylated siloxane (® Silvet Y-12867, WITCO) | 2.5 |
| Polyethylene glycol dimethacrylate (M$_n$ = 5000 g/mol) | 10 |
| t-Butanol | 500 |
| AIBN | 2 |

The polymer was prepared by the precipitation method in tert-butanol. The monomers in t-butanol were introduced as an initial charge and the reaction mixture was rendered inert, and then, after initial heating, the reaction was initiated by addition of AIBN. The polymer was isolated by removing the solvent under suction and by subsequent vacuum drying.

EXAMPLE 8

| Reactants | amount (g) |
|---|---|
| NH$_3$-neutralized AMPS | 10 |
| Acrylamide | 20 |
| Polyglycol-B-1100-methacrylate | 7.5 |
| N-2-Vinylpyrrolidone | 30 |
| t-Butanol | 500 |
| Dilauroyl peroxide | 2 |

The polymer was prepared by the precipitation method in tert-butanol. The monomers in t-butanol were introduced as an initial charge and the reaction mixture was rendered inert, and then, after initial heating, the reaction was initiated by addition of DLP. The polymer was isolated by removing the solvent by evaporation and by subsequent vacuum drying.

EXAMPLE 9

| Reactants | amount (g) |
|---|---|
| NH$_3$-neutralized AMPS | 60 |
| Diallyldimethylammonium chloride (DADMAC) | 10 |
| [2-(Methacryloyloxy)ethyl]trimethylammonium chloride | 10 |
| ® Genapol-LA-250-crotonate | 10 |
| Isopropanol | 300 |
| Water | 200 |
| ABAH | 2 |
| Poly[acrylic acid-co-N-vinylformamide] | 7 |

The polymer was prepared by the solution method in an isopropanol/water mixture. The monomers were introduced in isopropanol/water, the reaction mixture was rendered inert, and then, after initial heating, the reaction was initiated by addition of ABAH. The polymer was isolated by removing the solvent mixture by evaporation and by subsequent vacuum drying.

EXAMPLES 10 to 18

Examples 10 to 18 show the effect of synergistic additives on the viscosity behavior of selected copolymers. By this means it is demonstrated that the threshold temperature and the extent of the thermoassociative effect can be controlled within wide limits. Examples 10 and 15 are comparative examples. The viscosities were determined at up to 100° C. with a Brookfield viscometer and at up to 200° C. with a Fann 50 viscometer. For the purpose of simplification the only temperatures indicated here are those at which a significant viscosity increase was observed ($T_{visc}$ column) and the maximum viscosity observed (maximum viscosity column)

TABLE 1

Examples 10 to 18

| Ex. | Copolymer | Amount of copolymer [% by wt.] | Synergistic additive | Amount of synergistic additive [% by wt.] | Sea salt [% by wt.] | $T_{visc}$ [° C.] | Maximum viscosity [mPas] |
|---|---|---|---|---|---|---|---|
| 10 | Example 2 | 2 | ® Genapol LA 070 | 0 | 3.3 | Not measurable | 15 |
| 11 | Example 2 | 2 | ® Genapol LA 070 | 1 | 3.3 | 91 | 260 |
| 12 | Example 2 | 2 | ® Genapol LA 070 | 2 | 3.3 | 82 | 1200 |
| 13 | Example 2 | 2 | ® Genapol LA 070 | 4 | 3.3 | 65 | >1500 |
| 14 | Example 2 | 2 | ® Genapol LA 200 | 2 | 3.3 | 93 | 950 |
| 15 | Example 8 | 2 | Polyglycol-B-1100 | 0 | 3.3 | Not measurable | 20 |
| 16 | Example 8 | 2 | ® Genapol LA 070 | 2 | 3.3 | 98 | 530 |
| 17 | Example 8 | 2 | Polyglycol-B-1100 | 2 | 3.3 | 118 | 610 |
| 18 | Example 8 | 2 | Polyglycol-B-1100 | 2 | 0 | 153 | 420 |

The ®Genapol products are alkylpolyglycols from Clariant GmbH.

Comparative examples 10 and 15 show that without the addition of a synergistic additive no measurable thermoassociative effect is observed.

Examples 10 to 13 document the effect of the amount of synergistic additive used on the threshold temperature of the thermoassociation and on its maximum viscosity.

Example 14 shows that different additives for a given copolymer also alter the threshold temperature, and also the viscosity.

The nature and functionality of the polymer of the invention, as shown by comparing examples 12 and 16, likewise has a marked influence on the viscosity. Example 18 illustrates how the thermoassociative properties can be controlled by way of the salt content of the compositions.

What is claimed is:
1. A method for controlling the threshold temperature and the extent of the thermoassociative effect in a media, said method comprising adding to the media
   I) at least one water-soluble or water-swellable copolymer obtained by free-radical copolymerization of

A) 50 to 99.5 weight percent acryloyldimethyltaurine or acryldimethyltaurate and mixtures thereof, based on the copolymer wherein the acryldimethyltaurine or acryloyldimethyltaurate is more than 80 percent neutialized, F) one or more, macromonomer having a number-average molecular weight of greater than or equal to 200 g/mol, and at least one structural element selected from the group consisting of B) one or more elementally unsaturated, noncationic, comonomer containing at least one oxygen, nitrogen, sulfur or phosphorus atom and possessing a molecular weight of less than 500 g/mol, C) one or more olefinically unsaturated, cationic, comonomer containing at least one oxygen, nitrogen, sulfur or phosphorus atom and possessing a molecular weight of less than 500 g/mol.

D) one or more at least monofunctional, silicon-containing component capable of free-radical polymerization, and E) one or more at least monofunctional, fluorine-containing components capable of free-radical polymerization, wherein the copolymerization takes place in the presence or the absence of at least one polymeric additive having number-average molecular weights of from 200 g/mol to $10^9$ g/mol, and wherein at least one structural element selected from component B) to F) possesses heat-sensitive properties;

II) at least ore synergistic additive selected from the group consisting of an anionic surfactant, cationic surfactant, nonionic surfactant, betaine surfactant and mixtures thereof, and III) from 0.1 to 25 percent by weight of a salt.

2. The method of claim 1, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphoric acid or the esters or salts thereof; vinylsulfonic acid or the esters or salts thereof, aliylphosphonic acid or the esters or salt there of, methallylsulforic acid or the esters or salts thereof, and mixtures thereof.

3. The method of claim 1, wherein the comonomer C) is selected from a group consisting of diallyldimethylammonium chloride,
[2-(methacryloyloxy)ethyl]trimethylammonium chloride,
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride and/or
N-methyl4-vinylpyridinium chloride, and mixtures thereof.

4. The method of claims 1, wherein the silicon-containing component D) is a compounds of the formula (I)

$$R^1\text{—}Y\text{—}[(Si(R^3R^4)\text{—}O\text{—})_w\text{—}(Si(R^5R^6)\text{—}O)_x\text{—}]\text{—}R^2 \quad (I)$$

where
$R^1$ is a polymerizable function of a vinylically unsaturated compound;
Y is a chemical bridge,
$R^3$, $R^4$, $R^5$, and $R^6$ independently of one another are —$CH_3$, —O—$CH_3$, —$C_6H_5$ or —O—$C_6H_5$;
w and x denote numbers from 0 to 500, it being necessary for either w or x to be greater than zero; and
$R^2$ is a saturated or unsaturated aliphatic, cycloaliphatic, arylaliphatic or aromatic radical having in each case 1 to 50 carbon atoms or a group of the formulae —OH, —$NH_2$, —$N(CH_3)_2$, —$R^7$ or a group —Y—$R^1$, where $R^7$ is an Si-containing group.

5. The method of claim 1, wherein the fluorine-containing components E) are compounds of the formula (II)

$$R^1\text{—}Y\text{—}O\text{—}C_rH_{2r}C_sF_{2s}CF_3 \quad (II)$$

where
$R^1$ represents a polymerizable function from a vinylically unsaturated compound;
Y is a chemical bridge; and
r and s are stoichiometric coefficients which independently of one another denote numbers from 0 to 200.

6. The method of claim 1, wherein the macromonomers F) are compounds of the formula (III)

$$R^1\text{—}Y\text{—}[(A)_v\text{—}(B)_w\text{—}(C)_x\text{—}(D)_z]\text{—}R^2 \quad (III)$$

where $R^1$ is a polymerizable function from a vinylically unsaturated compound;
Y is a bridging group;
A, B, C, and D independently of one another are discrete chemical repeating units;
v, w, x, and z independently of one another amount to from 0 to 500, the sum of v, w, x, and z being on average $\geq 1$; and
$R^2$ is a linear or branched aliphatic, olefinic, cycloaliphatic, arylaliphatic or aromatic $(C_1–C_{50})$ hydrocarbon radical, OH, —$NH_2$ or —$N(CH_3)_2$ or is [—Y—$R^1$].

7. The method of claim 1, wherein the polymeric additive is selected from the group consisting of polyalkylene glycol, alkylpolyglycol, and mixtures thereof or a homopolymer or copolymer selected from the group consisting of N-vinylformamide, N-vinylacetamide, N-vinylpyrrolidone, ethylene oxide, propylene oxide, acryloyldimethyltaurine, N-vinylcaprolactone, N-vinylmethylacetamide, acrylamide, acrylic acid, methacrylic acid, N-vinylmorpholide, hydroxymethyl methacrylate, diallyldimethylammonium chloride (DADMAC) and/or [2-(methacryloyloxy)ethyl]trimethylammonium chloride (MAPTAC), and mixtures thereof.

8. The method of claim 1, wherein the copolymer is crosslinked.

9. The method of claim 1, wherein said copolymerization is precipitation polymerization in tert-butanol.

10. The method of claim 1, wherein the synergistic additive is selected from the group consisting of polyalkylene glycols, alkylpolyglycols, ether sulfates, alkyl quats, cocoamidopropylbetaine, ether sulfate/betaine mixtures, and mixtures thereof.

11. The method of claim 10, wherein the synergistic additive is selected from the group consisting of polyethylene glycol (PEG), methoxypolyethylene glycol (MPEG), and mixtures thereof, said polyethylene glycol and/or methoxypolyethylene glycol having a molecular weight of more than 300 g/mol and/or water-soluble alkylpolyglycols having $(C_4–C_{22})$-alkyl chains.

12. The method of claim 1, wherein the weight ratio of copolymers to synergistic additives is from 1:1 000 to 1 000:1.

13. The method of claim 1, wherein the media is selected from the group consisting of oilfields, chemicals, cosmetic compositions, dermatological compositions, pharmaceutical compositions, detergent and crop protection formulations.

14. The method of claim 4, wherein $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

15. The method of claim 4, wherein the chemical bridge, Y, is selected from the group consisting of —O—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$–C$_{50}$)alkyl-O—, —O-phenyl-O—, —O-benzyl-O—, —O—(C$_5$–C$_8$)cycloalykl-O—, —O—(C$_1$–C$_{50}$)alkenyl-O—, —O—(CH(CH$_3$)—CH$_2$—O)$_n$—, —O—(CH$_2$—CH$_2$—O)$_n$—, and —O—([CH—CH$_2$—O]$_n$—[CH$_2$—CH$_2$—O]$_m$)$_o$—, where n, m, and o independently of one another denote numbers from 0 to 200.

16. The method of claim 4, wherein $R^7$ is selected from the group consisting of —O—Si(CH$_3$)$_3$, —O—Si(phenyl)$_3$, —O—Si(O—Si(CH$_3$)$_8$)$_2$CH$_3$), —O—Si(O—Si(phenyl)$_3$)$_2$phenyl), and mixtures thereof.

17. The method of claim 5, wherein $R^1$ is a radical selected from the group consisting of vinyl, allyl, methyl, methylvinyl, acryloyl, methacryloyl, crotonyl, senecionyl, itaconyl, maleyl, fumaryl, styryl, and mixtures thereof.

18. The method of claim 5, wherein the chemical bridge, Y, is selected from the group consisting of —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$–C$_{50}$)alkyl-O—, —O-phenyl-O—, —O-benzyl-O—, —O—(C$_5$–C$_8$)cycloalykl-O—, —O—(C$_1$–C$_{50}$)alkenyl-O—, —O—(CH(CH$_3$)—CH$_2$—O)$_n$—, —O—(CH$_2$—CH$_2$—O)$_n$—, and —O—([CH—CH$_2$—O]$_n$—[CH$_2$—CH$_2$—O]$_m$)$_o$—, where n, m, and o independently of one another denote numbers from 0 to 200.

19. The method of claim 6, wherein $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

20. The method of claim 6, wherein the bridging group Y is selected from the group consisting of O—, —S—, —C(O)—, —C(O)—O—, —O—CH$_2$—CH(O—)—CH$_2$OH, —O—CH$_2$—CH(OH)—CH$_2$O—, —O—SO$_2$—O—, —O—SO$_2$—O—, —O—SO—O—, —PH—, —P(CH$_3$)—, —PO$_3$—, —NH—, —N(CH$_3$), and mixtures thereof.

21. The method of claim 6, wherein the repeating units A, B, C, and D originate from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, diiopropylacrylamide, and mixtures thereof.

22. The method of claim 6, wherein the repeating units A, B, C, and D originate from ethylene oxide and/or propylene oxide.

23. The method of claim 6, wherein v, w, x, and z independently of one another amount to from 1 to 30.

24. The method of claim 1, wherein the synergistic additive is an alkyl ether sulfate.

25. The method of claim 1, wherein the synergistic additive is a lauryl ether sulfate.

26. The method of claim 1 wherein the synergistic additive is an behenyl quat.

27. The method of claim 1, wherein the synergistic additive is an ether sulfate/betaine mixture.

28. The method of claim 12, wherein the weight ratio of said copolymer to synergistic additive is from 1:100 to 100:1.

29. The method of claim 12, wherein the weight ratio of said copolymer to synergistic additive is from 1:10 to 10:1.

30. The method of claim 1, wherein the at least one water-soluble or water-swellable copolymer is obtained by free-radical copolymerization of components A, F and B in the absence of at least one polymeric additive having number-average molecular weights of from 200 g/mol to $10^9$ g/mol and said synergistic additive is an alkylpolyglycol.

31. The method of claim 1, wherein the at least one water-soluble or water-swellable copolymer is obtained by free-radical copolymerization of components A, F and B in the presence of at least one polymeric additive having number-average molecular weights of from 200 g/mol to $10^9$ g/mol and said synergistic additive is an alkylpolyglycol.

32. The method of claim 1, wherein the salt is sodium chloride.

33. The method of claim 1, wherein the one or more olefinically unsaturated, noncationic comonomer B) is heat sensitive.

* * * * *